United States Patent
Hille et al.

(10) Patent No.: US 9,308,202 B2
(45) Date of Patent: Apr. 12, 2016

(54) TRANSDERMAL THERAPEUTIC SYSTEM FOR ADMINISTERING THE ACTIVE SUBSTANCE BUPRENORPHINE

(75) Inventors: Thomas Hille, Koblenz (DE); Michael Horstmann, Neuwied (DE); Walter Mueller, Andernach (DE)

(73) Assignee: PURDUE PHARMA L.P., Stamford, CT (US)

( * ) Notice: Subject to any disclaimer, the term of this patent is extended or adjusted under 35 U.S.C. 154(b) by 808 days.

(21) Appl. No.: 12/515,848

(22) PCT Filed: Nov. 7, 2007

(86) PCT No.: PCT/EP2007/009622
§ 371 (c)(1),
(2), (4) Date: Jan. 12, 2010

(87) PCT Pub. No.: WO2008/061625
PCT Pub. Date: May 29, 2008

(65) Prior Publication Data
US 2010/0119585 A1 May 13, 2010

(30) Foreign Application Priority Data
Nov. 21, 2006 (DE) .......................... 10 2006 054 731

(51) Int. Cl.
*A61K 31/485* (2006.01)
*A61K 9/70* (2006.01)

(52) U.S. Cl.
CPC ............. *A61K 31/485* (2013.01); *A61K 9/7084* (2013.01); *A61K 9/7092* (2013.01)

(58) Field of Classification Search
CPC ............ A61K 2300/00; A61K 31/485; A61K 31/4468; A61K 9/7023; A61K 9/0014; A61K 9/7084; A61K 9/7092; A61K 47/12; A61K 9/7038; A61K 8/37; A61K 47/14
See application file for complete search history.

(56) References Cited

U.S. PATENT DOCUMENTS

| | | | |
|---|---|---|---|
| 3,433,791 A | 3/1969 | Bentley | |
| 4,806,341 A * | 2/1989 | Chien et al. | 424/448 |
| 5,240,711 A | 8/1993 | Hille et al. | |
| 5,968,547 A | 10/1999 | Reder | |
| 6,264,980 B1 * | 7/2001 | Hille | 424/449 |
| 6,344,212 B2 | 2/2002 | Reder et al. | |

(Continued)

FOREIGN PATENT DOCUMENTS

| | | |
|---|---|---|
| DE | 39 39 376 | 5/1991 |
| DE | 199 58 554 | 1/2001 |

(Continued)

OTHER PUBLICATIONS

Rustan et al. "Fatty acids: Structure and Properties", Encyclopedia of Life Science, 2005.*

(Continued)

*Primary Examiner* — Isis Ghali
(74) *Attorney, Agent, or Firm* — Jones Day

(57) ABSTRACT

The invention relates to a transdermal therapeutic system for administering the active substance buprenorphine. Said system comprises at least one carboxylic acid that determines the solubility of buprenorphine in the matrix layer and that can likewise be absorbed. The transdermal therapeutic system according to the invention is used in the treatment of pain and is characterized by a considerably increased utilization of the active substance.

20 Claims, 1 Drawing Sheet

(56) References Cited

U.S. PATENT DOCUMENTS

| | | | |
|---|---|---|---|
| 6,783,769 | B1 | 8/2004 | Arth et al. |
| 7,390,500 | B2 | 6/2008 | Müller |
| 2001/0002259 | A1 | 5/2001 | Reder et al. |
| 2004/0126416 | A1 | 7/2004 | Reidenberg et al. |
| 2004/0202710 | A1 | 10/2004 | Muller |
| 2004/0228906 | A1 | 11/2004 | Bartholomaeus |
| 2005/0118245 | A1 | 6/2005 | Wilsmann |
| 2005/0191340 | A1 | 9/2005 | Bartholomaeus et al. |
| 2006/0148364 | A1 | 7/2006 | Pohlmann |
| 2008/0113013 | A1 | 5/2008 | Koch |
| 2014/0363487 | A1 | 12/2014 | Hille |
| 2015/0306093 | A1 | 10/2015 | Wauer |

FOREIGN PATENT DOCUMENTS

| | | | |
|---|---|---|---|
| DE | 10 2004 062 647 | | 6/2006 |
| DE | 10 2004 062614 | | 7/2006 |
| EP | 368409 | A * | 5/1990 |
| EP | 0 430 019 | | 6/1991 |
| EP | 0 430 019 | B1 | 3/1996 |
| EP | 1 572 167 | | 9/2005 |
| EP | 0 964 677 | | 8/2006 |
| EP | 1 731 152 | | 12/2006 |
| GB | 1136214 | | 12/1968 |
| JP | 2000-511936 | A | 9/2000 |
| JP | 2003-503445 | | 1/2003 |
| JP | 2003-522144 | | 7/2003 |
| RU | 2251413 | | 5/2005 |
| RU | 2005132834 | A | 4/2006 |
| WO | WO 96/19975 | | 7/1996 |
| WO | WO 98/36728 | | 8/1998 |
| WO | WO 98-36728 | | 8/1998 |
| WO | WO 01/01967 | | 1/2001 |
| WO | WO 01/58447 | | 8/2001 |
| WO | WO 02/41878 | | 5/2002 |
| WO | WO 03/018071 | | 3/2003 |
| WO | WO 03/079962 | | 10/2003 |
| WO | WO 2004-014336 | | 2/2004 |
| WO | WO 2004/014336 | | 2/2004 |
| WO | WO 2004/054553 | A1 | 7/2004 |
| WO | WO 2006/030030 | | 3/2006 |
| WO | WO 2014/195352 | A1 | 12/2014 |

OTHER PUBLICATIONS

Roy et al. "Transdermal Delivery of Buprenorphine through Cadaver Skin", Journal of Pharmaceutical Sciences, vol. 83, No. 2, Feb. 1994.*

Chien "Transdermal Controlled System Medications", Marcel Dekker Inc., 1987, pp. 36-45.

European Pat Appln. 12 826 670.7 (based on PCT Application No. PCT/IB2012/002973)—Third party submission dated May 24, 2015.

European Pat. Appln. No. 14 171 110.1 (Pub. No. 2 810 646) (corresponds to PCT Application No. PCT/EP2014/061567)—Response to Third Party Submission dated Jun. 12, 2015.

European Pat. Appln. No. 14 171 110.1 (Pub. No. 2 810 646) (corresponds to PCT Application No. PCT/EP2014/061567)—Third Party Submission dated May 8, 2015.

European Pat. Appln. No. 14 171 110.1 (Pub. No. 2 810 646) (corresponds to PCT Application No. PCT/EP2014/061567)—Communication re: European Search Report dated Aug. 21, 2014.

Fachinformation Transtec, 2001, Bundesverband der Pharmazeutishen Inudtrie e.V. (in German w/ English translation).

Gebrauchsinformation: Information für den Anwender, Transtec 35 Mikrogramm/h—transdermales Pflaster, Version 5.0m Nov. 18, 2010 (in German with English translation of p. 8, last paragraph (item 6) to p. 9, first paragraph of the Summary of Product Characteristics of Transtec 35 micrograms/hr (Transtec SPC)).

Highlights of Prescribing Information—Butrans (buprenorphine) Transdermal System—Aug. 2010.

Highlights of Prescribing Information—Butrans (buprenorphine) Transdermal System—Jun. 2010.

Kandavilli, S. "Polymers n Transdermal Drug Delivery Systems", Pharmaceutical Technology, May 2002.

Merck Index "An encyclopedia of chemicals, drugs, and biological",15th Edition, p. 264 (buprenorphine).

Napp Pharmaceuticals Limited, BuTrans 5, 10 and 20 ug/h Transdermal Patch—Summary of Product Characteristics, Mar. 11, 2010.

PCT Application No. PCT/EP2007/09622—International Preliminary Report on Patentability (IPRP) and Written Opinion of IPRP (WO-IPRP) from EPO as International Search Authority (in German) dated Jun. 10, 2009 (with English translation).

PCT Application No. PCT/EP2007/09622—International Search Report dated Jul. 18, 2008.

PCT Application No. PCT/EP2013/076325—International Search Report (ISR) and Written Opinion from EPO as International Search Authority dated May 13, 2014.

PCT Application No. PCT/EP2013/076325—International Preliminary Report on Patentability dated Jun. 16, 2015 with Written Opinion from EPO as International Search Authority.

PCT Application No. PCT/EP2014/061567—International Search Report (ISR) and Written Opinion from EPO as International Search Authority dated Aug. 21, 2014.

PCT Application No. PCT/IB2012/002973—International Preliminary Report on Patentability (IPRP) and Written Opinion from EPO as International Search Authority, Jun. 17, 2014.

Posker, GL "Buprenorphine 5, 10 and 20 µg/h Transdermal Patch—A review of Its Use in the Management of Chronic Non-Malignant Pain," Adis International Ltd, , Drugs, Dec. 1, 2011, 71(18) 2491-2509.

Transdermanye terapevti' cheskie sistemy (Transdermal Therapeutic System), http://medi.ru/doc/991011.htm, 2001 (in Russion with English translation).

Transtec 35, 52.5 and 70 micrograms transdermal patch—Summary of Product Characteristics, Nov. 10, 2014.

Chilean Appln. No. 001559-2014—Notification of Oppositions dated Jan. 23, 2015 (in Spanish with English translation).

Chilean Appln. No. 001559-2014—Opposition dated Dec. 2, 2014 by Asociacion Industrial de Laboratorios Farmaceuticos AG (in Spanish with English translation).

Chilean Appln. No. 001559-2014—Opposition dated Dec. 9, 2014 by Laboratorios Recalcine SA (in Spanish with English translation).

Chilean Appln. No. 001559-2014—Response with attachments dated Mar. 23, 2015 to Oppositions by Asociacion Industrial de Laboratorios Farmaceuticos AG and Laboratorios Recalcine SA (in Spanish with English translation of Response).

Colombian Appln. No. 14.149.730—Opposition by Laboratorio Franco Colombiano SAS Lafrancol SAS, publication in Gazette 700 dated Jul. 21, 2014 (in Spanish with English translation).

Colombian Appln. No. 14.149.730—Response dated Jan. 21, 2015 to Opposition by Laboratorio Franco Colombiano SAS Lafrancol SAS (in Spanish with English translation).

Correa, Carlos, "Pautas para el examen de patentes farmaceuticas. Una perspectiva desde Ia Salud Publica" ("Guidelines for the examination of pharmaceutical patents" Developing a public health perspective), Universidad de Buenos Aires, Mar. 2008 (in Spanish with English translation of Foreword, pp. vii-viii).

ROMPP Online, Version 3.27, "Emulsionen", Sep. 6, 2012, Angsgar Behler (ed.) (in German with English translation).

Falbe, J., Rompp Chemie Lexikon, (1990), Georg Thieme Verlag Stuttgart, pp. 1158-1159 (in German with English translation).

* cited by examiner

TRANSDERMAL THERAPEUTIC SYSTEM FOR ADMINISTERING THE ACTIVE SUBSTANCE BUPRENORPHINE

The present invention relates to a transdermal therapeutic system with at least one carboxylic acid which determines the solubility of the buprenorphine in the matrix layer and is likewise absorbable, for pain therapy, with significantly increased active ingredient utilization.

The active ingredient buprenorphine (17-(cyclopropyl-methyl)-α-(1,1-dimethylethyl)-4,5-epoxy-18,19-dihydro-3-hydroxy-6-methoxy-α-methyl-6,14-ethenomorphinan-7-methanol) is a partially synthetic opiate whose advantage over other compounds from this class of substance lies in a higher activity. This means that freedom from pain can be achieved in cancer or tumour patients with very unfavourable diagnosis, in the final stage, with daily doses of around 1 mg. A feature of buprenorphine in this context over the synthetic opioid fentanyl and its analogues is that the addictive potential of buprenorphine is lower than that of these compounds. The disadvantage is that, owing to the high molecular weight of buprenorphine, namely 467.64 daltons, it is difficult to effect its transdermal absorption.

In spite of this, transdermal systems containing buprenorphine (e.g. Transtec® or Norspan®) are already available commercially. German Patent DE 39 39 376 C1 describes their functioning. The active ingredient is in homogeneous solution in a polyacrylate matrix, with a carboxylic acid serving as permeation enhancer and solubilizer.

Systems in which the active ingredient is in homogeneous solution are commonly distinguished by low active substance utilization. The reason for this is that the thermodynamic activity of the active ingredient, which determines the delivery of active ingredient, decreases in the course of administration, as a result of the falling active ingredient loading. Uniform delivery of active ingredient over the entire administration time is achievable only through a relatively high active ingredient loading in comparison to the amount that is to be delivered. The published data for the Transtec® 35 product, which is marketed in Europe, suggest, for example, active ingredient utilization of only 17% over the administration period. Given that buprenorphine is an expensive active ingredient, higher active ingredient utilization would be a substantial advantage from a costs standpoint. A very low loading of the system with the buprenorphine, which is a narcotic, and a resultant minimal residual content following application in the systems used, moreover, is very desirable from the standpoint of safety.

It was an object of the present invention, therefore, to develop a TTS which makes the active ingredient buprenorphine, whose transdermal absorption is difficult to effect, available to transdermal administration, with significantly increased active ingredient utilization.

This object is achieved in accordance with the invention, and in a surprising way, by means of a transdermal therapeutic system for administering buprenorphine to the skin, the TTS comprising an active-ingredient-impermeable backing layer, at least one pressure-sensitive adhesive matrix layer, comprising the active ingredient buprenorphine and at least one carboxylic acid, and, if desired, a protective layer which is to be detached before use. The matrix layer is constructed on the basis of polysiloxanes or polyisobutylene. The buprenorphine is in solution in the carboxylic acid or the carboxylic acids, and this solution is in dispersion in the form of droplets in the matrix layer. This is all the more surprising in view of the fact that buprenorphine, on account of its known physicochemical properties, more particularly its poor solubility, its comparatively high melting point of 216° C., and, as already mentioned, its high molecular weight, tends readily towards crystallization. For this reason a solvent with at least one acidic group is used in order to prevent the buprenorphine crystallizing during the storage of the pharmaceutical form. Both buprenorphine itself and carboxylic acids have an extremely low solubility in polysiloxanes or polyisobutylene. As a consequence of this it is possible to dissolve buprenorphine in a carboxylic acid and to disperse this solution in the form of droplets in a matrix layer prepared on the basis, as base polymer, of polyisobutylene or of polysiloxanes, preferably amine-resistant dimethyl-polysiloxanes, more preferably a mixture of an amine-resistant and a non-amine-resistant dimethyl-polysiloxane, the non-amine-resistant dimethyl-polysiloxane being present at not more than 40% by weight, preferably 2% to 20% by weight. In this case it is important that the mixture of buprenorphine and carboxylic acid or carboxylic acids is in liquid form.

The carboxylic acids employed are typically of sparing solubility in the organic solvents of the adhesives. Consequently the liquid mixture of buprenorphine and carboxylic acid can be dispersed in the solution of the adhesive, with the dispersion being retained following removal of the solvent. In a matrix layer of this kind, the solubility of the buprenorphine is dependent virtually only on the amount of the carboxylic acid or carboxylic acids. The amount of the dispersed solution can be up to 40% by weight, it being preferred not to exceed 20% by weight. The droplet size itself ought preferably not to exceed 50 μm. The preferred size is dependent, furthermore, on the thickness of the matrix layer.

Figure 1:
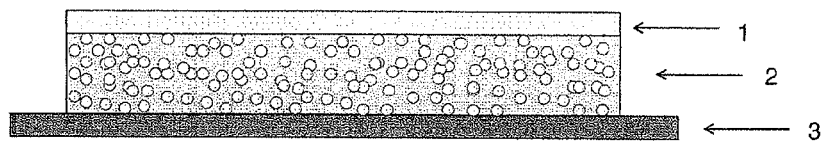
FIG. 1 shows a diagrammatic representation of a one-layer self-adhesive system of this kind.

1 backing layer
2 matrix layer based on polysiloxanes with disperse droplets of a buprenorphine/carboxylic acid solution
3 protective layer to be removed before use
4 skin contact layer based on a polyacrylate adhesive
5 pressure-sensitive adhesive layer without buprenorphine
6 backing layer (e.g. skin-coloured)

Since carboxylic acids can likewise be absorbed through the skin, their amount in the system goes down during the time of application, and hence there is also a reduction in the saturation solubility of the buprenorphine. As a result of this, the decrease in the thermodynamic activity of buprenorphine, as is caused by the delivery, is compensated. The choice of the carboxylic acid is guided by the absorption through the skin, which is just as quick, and preferably quicker, as compared with that of buprenorphine. It is preferred to use carboxylic acids which are liquid at skin temperature. The carboxylic acid or the carboxylic acids is or are selected from the group consisting of oleic acid, laevulinic acid, linoleic acid and linolenic acid. Given an appropriate embodiment it is possible to achieve supersaturated states during the time of application. In supersaturated systems the thermodynamic activity of the active ingredient and hence also the permeation rate per unit area is increased in accordance with the supersaturation factor. As a result, advantageously, it is possible to minimize the delivery area and also the area of the system. During storage, both buprenorphine and the acid remain in the polymer matrix, so that during this time the system is not more than saturated, and recrystallization of the active ingredient is ruled out.

A further aspect of the invention concerns the effect that in systems of this kind, if the delivery of the acid is too quick, the rise in the thermodynamic activity can lead to an excessive increase in the permeation rate following application. The consequence is that the TTS becomes prematurely exhausted as a result of excessively rapid delivery of active ingredient. It has now been found that this kind of effect is prevented by addition of a further layer based on polyacrylates. This layer is located preferably between the polymer matrix layer, containing active ingredient, and the skin, or else between matrix layer and backing layer. This additional layer is preferably embodied as a self-adhesive skin contact layer.

The solubility of buprenorphine in polyacrylates is significantly higher than in polysiloxanes or polyisobutylene and, depending on the precise composition, ranges up to about 10 percent by weight. Since, as a result, the overall system has a higher saturation solubility for buprenorphine, the degree of supersaturation occasioned by the delivery of the acid is reduced by redistribution of the buprenorphine from the matrix layer into the polyacrylate layer. As a result of this, the delivery of active ingredient is more uniform, and premature exhaustion of the system is prevented. It has been found that, in one preferred embodiment, with the matrix layer loaded with about 0.4 mg of buprenorphine and the carboxylic acid used being laevulinic acid, a skin contact layer with a coating weight of 15-30 g/m$^2$ is sufficient per cm$^2$ in order to achieve the desired effect.

There are basically no limitations in terms of the monomers used for producing the polyacrylate adhesive. On the basis of theoretical considerations, however, preference is given to adhesives without free carboxyl groups, since they are unable to immobilize the basic buprenorphine via formation of salts.

Figure 2:
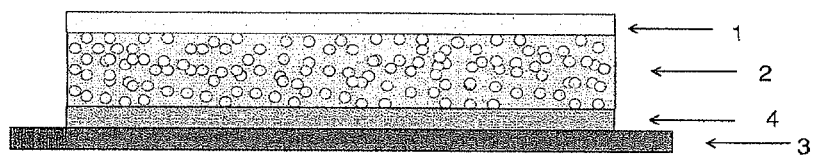
FIG. 2 depicts a system with a skin contact layer.
Figure 3:
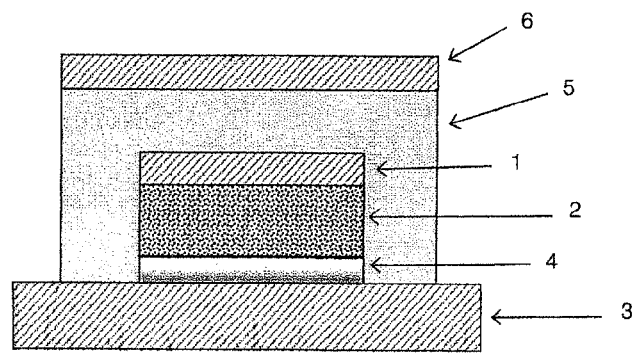
FIG. 3 shows a multilayer system with a top patch. In these figures the meaning of the reference numerals is as follows.

FIG. 2 shows a diagrammatic representation of a system of this kind; its production is described in Example 1. The thickness of the matrix layer and skin contact layer must in each case be optimized as a function of the chosen active ingredient concentration in the matrix layer and, respectively, the amount of active ingredient per unit area. The amount or concentration of the acid in the matrix layer depends on its solvency for buprenorphine. In the case of the preferred use of laevulinic acid, buprenorphine and the acid are used in equal proportions by weight. The chosen concentration of both substances, of 7% to 9% by weight, has proved to be suitable, but can also be selected differently, taking appropriate account when selecting the coating weight, without affecting the performance of the TTS.

Transdermal therapeutic systems according to Example 1 were compared in a pharmacokinetics study in humans, with TTS already on the market, as a reference system. It was found that a 17 cm$^2$ system according to Example 1 with a buprenorphine content of 6.3 mg corresponds to a 25 cm$^2$ reference TTS having an active ingredient content of 20 mg. On the basis of the stated delivery of the reference product, of 35 µg/h TTS, this gives for the reference product an active ingredient utilization of 17% and for a TTS according to Example 1 an active ingredient utilization of 53%. This clearly shows that, with transdermal systems according to Example 1, the objective of substantially improved active ingredient utilization has been achieved. With the TTS of the invention containing buprenorphine as active ingredient, accordingly, it is possible to achieve in vivo active ingredient utilizations of at least 30%, preferably at least 40%, more preferably at least 50%. A further advantage arising is that these systems, on account of the higher permeation rate, can be used with a surface area of approximately 30% less that the reference systems.

A particular advantage is that this improved active ingredient utilization allows the loading of the system with the narcotic buprenorphine to be reduced further, with a consequent further minimization in the residual buprenorphine content in the spent systems after use.

The transdermal therapeutic systems of the invention can be provided with different release profiles and in different dose strengths. As already described above, for example, the active ingredient release profile can be influenced by means, for example, of appropriate variation to the layer thickness of the active-ingredient-containing matrix and/or the skin contact layer, or by altering the concentration of active ingredient in the matrix. The dose strength of the TTS of the invention can be modified, for example, by varying the surface area of the active-ingredient-containing matrix, while keeping the composition and layer thickness of the matrix and skin contact layer the same, in order thus to obtain different dose strengths. In this way it is possible, preferably, to obtain transdermal therapeutic systems which have properties comparable with those of transdermal therapeutic systems already on the market.

Through the provision of TTS with different dosage levels it is possible to put a patient individually on the amount of active ingredient he or she requires. Furthermore, it becomes possible to set up the delivery of active ingredient to the patient in such a way that he or she is given the amount of active ingredient he or she needs, in a way which is known in principle, by means of an appropriate dosage scheme. In such a scheme, the amount of active ingredient administered to the patient is increased accordingly by means, for example, of sequential administration of transdermal therapeutic systems with different dose strengths. The sequential increase in the dose of active ingredient allows a further reduction in the side effects which it is known can possibly arise in the course of administration of the active ingredient buprenorphine. Examples of the sequential adaptation of the delivery of active ingredient to a patient by means of appropriate dosing schemes are described in, for example, patent applications WO 2006/030030 A2 and EP 1572167. The present invention hence also encompasses systems, kits for example, which comprise two or more TTS of the invention with different dose strengths.

The form taken by the transdermal therapeutic systems of the invention may be such as to allow subdivision of the TTS into different sub-units. Such divisibility likewise allows further modification of the TTS to the individual active ingredient requirement of a patient, or the use of the TTS for implementation of an appropriate dosing scheme. In this case the divisible TTS advantageously contains a multiplicity of polymer matrix regions which are separated spatially by regions free of active ingredient. The TTS can then be divided along the regions free of active ingredient, by cutting for example, so that one or more polymer matrix regions are separated off from the rest of the TTS. Examples of the construction of divisible TTS variants are described in, for example, patent applications WO 2003/079962 A2 and WO 02/41878 A2.

The transdermal therapeutic systems of the invention can be modified and used for different durations of administration. The TTS of the invention can for example each be applied for at least 12 h or 24 h. With preference, however, the individual TTS of the invention can also be used over a respective application duration of at least 72 h, 84 h or 96 h. Longer application durations, however, are also possible, such as 120 h, 144 h or 168 h, for example.

The invention is illustrated by the examples below, but without thereby restricting the scope of the invention:

EXAMPLE 1

A In a stainless steel vessel, 3.65 kg of buprenorphine are suspended in 3.65 kg of laevulinic acid and 2.6 kg of ethanol. With stirring, 60.6 kg of a polysiloxane adhesive in the form of a solution in n-heptane having a solids content of 74% by weight and 9.72 kg of heptane are added. The mixture is stirred until the buprenorphine base is fully dissolved, to give 80.22 kg of a buprenorphine-containing adhesive solution with 4.55% of buprenorphine, with a solids content of 64.8% (adhesive solution 1).

B For the skin contact layer, a polyacrylate adhesive prepared from 2-ethylhexyl acrylate, vinyl acetate and 2-hydroxyethyl acrylate is used. 31.87 kg of a solution of this adhesive, with a solids content of 51% by weight, is admixed with 6.5 kg of ethyl acetate and 1.91 kg of oleic acid, in pure form or as a mixture with other carboxylic acids, to give, following homogenization, approximately 40 kg of active-ingredient-free polyacrylate solution (adhesive solution 2).

C Auxiliary means known to the person skilled in the art are used to coat a film, which has been treated so as to be abhesive for the chosen adhesive, with the buprenorphine-containing adhesive solution 1. The coating thickness is chosen such that removal of the solvents results in a coating weight of the matrix layer of 55 g/m$^2$. The concentration of buprenorphine and laevulinic acid in this layer is 7% to 9% by weight. The backing layer of the subsequent system is then laminated onto the "dried" matrix layer. Adhesive solution 2 is likewise coated onto an abhesively treated film (the later protective film to be removed before the systems are used) and the organic solvents are removed. The coating thickness of the resulting skin contact layer ought to amount, following removal of the solvents, to approximately 20 g/m$^2$. The abhesively treated film is then removed from the matrix layer produced first, and the matrix layer is laminated onto the skin contact layer.

The individual systems can now be punched from the resulting total laminate.

In specific embodiments a TTS as described above can be provided with an over-plaster of larger surface area, preferably with rounded corners, comprising a pressure-sensitive adhesive matrix layer which is free of active ingredient and has a preferably skin-coloured backing layer. This is of advantage when the skin contact layer, on the basis of its physical properties alone, does not adhere sufficiently to the skin and/or when the buprenorphine-containing matrix layer, for the purpose of avoiding waste, has pronounced corners (square or rectangular shapes).

EXAMPLES 2-5

Production takes place in the same way as in Example 1, but with the concentrations and layer thickness of the matrix layer varied in accordance with Table 1.

EXAMPLE 6

As Example 6, the commercial product Transtec® from Grünenthal GmbH was used.

TABLE 1

Composition of the buprenorphine-containing TTS relative to the active ingredient matrix

| Example | Weight per unit area of matrix layer [g/m$^2$] | Buprenorphine content of matrix layer [% by weight] | Buprenorphine content [mg/cm$^2$] | Laevulinic acid content Laminate 1 [% by weight) |
|---|---|---|---|---|
| 1 | 55 | 7 | 0.385 | 7 |
| 2 | 60 | 7 | 0.42 | 7 |
| 3 | 65 | 8.4 | 0.546 | 8.4 |
| 4 | 80 | 7 | 0.56 | 7 |

Using these TTS, in vitro experiments were carried out with the Franz diffusion cell, which is known to a person skilled in the art, using epidermis from complete human skin. For this purpose, diecuts with an area of 2.54 cm$^2$ were punched from laminates, and were each tested against diecuts of the commercial product Transtec®. Transtec® is available commercially in three different dose strengths, which, however, are in proportion to their surface area. The concentrations of buprenorphine in the acceptor medium of the Franz cell were measured (Tab. 2). Additionally, after the experiment, the TTS were analysed for their buprenorphine and laevulinic acid content. The results of the analyses of Example 1 are shown in table and graph form alongside those of the further examples.

TABLE 2

Average cumulative quantities of buprenorphine, in micrograms/hour, released to the Franz cell from the TTS of the invention

| Example | 2 h | 4 h | 8 h | 24 h | 32 h | 48 h | 56 h | 72 h |
|---|---|---|---|---|---|---|---|---|
| 1 | <d.l.* | 0.015 | 0.118 | 1.79 | 3.40 | 7.56 | 13.6 | 21.1 |
| 2 | <d.l.* | 0.007 | 0.062 | 0.87 | 1.72 | 5.3 | 9.63 | 19.3 |
| 3 | 0.013 | 0.027 | 0.076 | 0.689 | 1.36 | 4.7 | 9.15 | 21.5 |
| 4 | 0.035 | 0.071 | 0.184 | 1.64 | 3.27 | 8.86 | 12.9 | 25.9 |
| Transtec ® | n.d. | 0.061 | 0.167 | 2.35 | n.d. | 11.4 | n.d. | 25.4 |

*<d.l. = below detection limit

When the cumulative flux rates from Table 2 are compared with one another, it is seen that all of the permeation rates of the TTS according to the invention are situated in the same order of magnitude as those of the commercial product Transtec®. Even if the Franz cell is not a substitute for clinical trials, but is instead used in order to discriminate between different TTS formulas, the results presented in Table 2 can be evaluated to show that, under in vitro conditions, TTS of Example 1 delivers just as much buprenorphine as Transtece. As already described above, a TTS according to Example 1 was compared, in a pharmacokinetics study in humans, with this TTS already on the market, as a reference system, and for the reference product an active ingredient utilization of 17% TTS was demonstrated, as compared with active ingredient utilization of 53% for a TTS according to Example 1.

After the permeation studies, all of the inventive example TTS were analysed for their residual laevulinic acid content. The residual amounts and the relative quantities of laevulinic acid delivered, as calculated from the residual amounts, are shown in Table 3.

TABLE 3

Release of laevulinic acid

| Example | Laevulinic acid content [mg/cm$^2$] | Residual laevulinic acid in the TTS [mg/cm$^2$] | Laevulinic acid released [%] |
|---|---|---|---|
| 1 | 0.385 | 0.025 | 93.5 |
| 2 | 0.42 | 0.026 | 93.8 |
| 3 | 0.546 | 0.033 | 94 |
| 4 | 0.56 | 0.039 | 93 |

Table 3 illustrates that, in accordance with the teaching of the invention, the TTS become depleted in laevulinic acid during use, and hence bring about the surprisingly high utilization of the active ingredient buprenorphine.

The invention claimed is:

1. A transdermal therapeutic system for administering buprenorphine to the skin, comprising:
    an active-ingredient-impermeable backing layer;
    at least one pressure-sensitive adhesive matrix layer comprising the active ingredient buprenorphine and laevulinic acid;
    wherein the matrix layer comprises a polymer selected from polysiloxanes or polyisobutylene;
    wherein the buprenorphine is dissolved in the laevulinic acid to form a solution and
    wherein the solution is dispersed, in the form of droplets, in the matrix layer.

2. The transdermal therapeutic system according to claim 1, wherein the polysiloxane is an amine-resistant dimethylpolysiloxane.

3. The transdermal therapeutic system according to claim 1, wherein the polysiloxane is a mixture of an amine-resistant and a non-amine-resistant dimethylpolysiloxane, in which the non-amine-resistant dimethylpolysiloxane is present at up to 40% by weight.

4. The transdermal therapeutic system according to claim 1, wherein the laevulinic acid diffuses into the skin inure quickly than does the active ingredient buprenorphine.

5. The transdermal therapeutic system according to claim 1, wherein the amount of the dispersed solution is up to 40% by weight.

6. The transdermal therapeutic system according to claim 1, wherein the laevulinic acid is liquid at skin temperature.

7. The transdermal therapeutic system according to claim 1, wherein buprenorphine and laevulinic acid are present in the same weight ratio.

8. The transdermal therapeutic system according to claim 1, wherein the matrix layer is in diffusible contact with a layer based on polyacrylates.

9. The transdermal therapeutic system according to claim 8, wherein the polyacrylate layer is embodied as a self-adhesive skin contact layer.

10. The transdermal therapeutic system according to claim 9, wherein the polyacrylate adhesive possesses no free carboxyl groups.

11. The transdermal therapeutic system according to claim 1, wherein active substance utilization under in vivo conditions of at least 30% is achieved.

12. A method of treating pain which comprises:
    administering to a patient, in need thereof, a transdermal therapeutic system for administering buprenorphine to the skin, wherein the transdermal therapeutic system comprises:
    an active-ingredient-impermeable backing layer;
    at least one pressure-sensitive adhesive matrix layer comprising a therapeutically effective amount of the active ingredient buprenorphine and laevulinic acid;
    wherein the matrix layer comprises a polymer selected from polysiloxanes or polyisobutylene;
    wherein the buprenorphine is dissolved in the laevulinic acid to form a solution; and
    wherein the solution is dispersed, in the form of droplets, in the matrix layer.

13. The transdermal therapeutic system according to claim 2,
    wherein the polysiloxane is a mixture of an amine-resistant and a non-amine-resistant dimethylpolysiloxane, where the non-amine-resistant dimethylpolysiloxane is present in the mixture at up to 40% by weight;
    wherein the laevulinic acid diffuses into the skin more quickly than does the active ingredient buprenorphine and where the laevulinic acid is liquid at skin temperature; and
    wherein the amount of the dispersed solution in the matrix layer is up to 40% by weight.

14. The transdermal therapeutic system according to claim 1, wherein active substance utilization under in vivo conditions of at least 40% is achieved.

15. The transdermal therapeutic system according to claim 1, wherein active substance utilization under in vivo conditions of at least 50% is achieved.

16. The transdermal therapeutic system according to claim 1, wherein the matrix layer comprises polyisobutylene.

17. The transdermal therapeutic system according to claim 1, wherein the droplets in the matrix layer consist essentially of the buprenorphine and the laevulinic acid.

18. The transdermal therapeutic system according to claim 1, wherein the matrix layer comprises polysiloxane.

19. The transdermal therapeutic system according to claim 1 further comprising a protective layer to be detached before use.

20. The method according to claim 12, wherein the matrix layer comprises polysiloxane.

* * * * *

UNITED STATES PATENT AND TRADEMARK OFFICE
CERTIFICATE OF CORRECTION

PATENT NO.        : 9,308,202 B2
APPLICATION NO.   : 12/515848
DATED             : April 12, 2016
INVENTOR(S)       : Thomas Hille, Michael Horstmann and Walter Mueller Page 1 of 1

It is certified that error appears in the above-identified patent and that said Letters Patent is hereby corrected as shown below:

In the claims

In claim 4 under column 7, line 40, the term "inure" should be replaced by "more".

Signed and Sealed this
Twenty-eighth Day of June, 2016

Michelle K. Lee
*Director of the United States Patent and Trademark Office*